(12) United States Patent
Zolotarsky et al.

(10) Patent No.: US 6,723,671 B2
(45) Date of Patent: Apr. 20, 2004

(54) FRAGRANCE EMITTING ARTICLE

(75) Inventors: Yelena Zolotarsky, Springfield, NJ (US); David O'Halloran, Milltown, NJ (US); Florence Bernard, Paris (FR); Pradeep Thaker, Howell, NJ (US)

(73) Assignee: Lavipharm Laboratories Inc., East Windsor, NJ (US)

( * ) Notice: Subject to any disclaimer, the term of this patent is extended or adjusted under 35 U.S.C. 154(b) by 168 days.

(21) Appl. No.: 09/835,098

(22) Filed: Apr. 13, 2001

(65) Prior Publication Data

US 2002/0151236 A1 Oct. 17, 2002

(51) Int. Cl.$^7$ ................................................ B32B 5/16
(52) U.S. Cl. .................... 442/417; 428/402.2; 442/149; 442/150; 442/151; 442/358; 442/409; 442/414
(58) Field of Search ..................... 239/36–56; 428/28, 428/36.1, 36.2, 36.4, 40.1, 40.2, 41.8, 42.1, 42.2, 42.3, 46, 54, 66.5, 141, 142, 143, 144, 190, 194–208, 219, 220, 221, 340, 343, 346, 352, 354, 355 RA, 357, 402, 402.2, 41.6, 147; 442/60, 70, 96, 118, 123, 124, 125, 149–151, 333, 358, 359, 400, 401–405, 409, 414, 408, 410, 411, 417, 443, 448, 450, 451, 452, 328, 329, 334, 364; 424/401–405, 408, 410, 411, 417, 443, 448, 450, 451, 452

(56) References Cited

U.S. PATENT DOCUMENTS

| | | | |
|---|---|---|---|
| 4,186,743 A | 2/1980 | Steiger | 128/284 |
| 4,419,396 A | 12/1983 | Sugimoto | 428/40 |
| 4,487,801 A | 12/1984 | Turnbull et al. | 428/313.5 |
| 4,528,226 A | 7/1985 | Sweeny | 428/40 |
| 4,606,956 A | 8/1986 | Charbonneau et al. | 428/40 |
| 4,661,388 A | 4/1987 | Charbonneau | 428/43 |
| 4,769,264 A | 9/1988 | Dreger | 428/40 |
| 4,774,133 A * | 9/1988 | Doree et al. | 428/304.4 |
| 4,880,690 A | 11/1989 | Szycher et al. | 428/224 |
| 4,988,557 A | 1/1991 | Charbonnean | 428/204 |
| 5,133,970 A | 7/1992 | Petereit et al. | 424/443 |
| 5,399,404 A | 3/1995 | Laughlin et al. | 428/40 |
| 5,512,277 A | 4/1996 | Uemura et al. | 424/8.03 |
| 5,591,146 A | 1/1997 | Hasse | 604/359 |
| 5,720,966 A | 2/1998 | Ostendorf | 424/402 |
| 5,733,272 A | 3/1998 | Brunner et al. | 604/359 |
| 5,951,534 A | 9/1999 | Cummings et al. | 604/359 |
| 6,063,397 A | 5/2000 | Fowler et al. | 424/443 |
| 6,077,821 A | 6/2000 | Morelli et al. | 512/25 |
| 6,132,830 A | 10/2000 | O'Halloran | 428/40.1 |
| 6,162,457 A | 12/2000 | Martz | 424/448 |
| 6,299,945 B1 * | 10/2001 | Mertz et al. | 427/208 |

\* cited by examiner

*Primary Examiner*—Arti R. Singh
(74) *Attorney, Agent, or Firm*—Dechert LLP; Thomas S. Deibert

(57) ABSTRACT

Fragrance emitting articles are provided along with methods of making and using the same. The fragrance emitting articles provided contain microcapsules of a fragrance, which microcapsules are associated with the fragrance emitting article without the addition of a binder. The invention also relates to methods of making the subject fragrance emitting articles and methods of using those articles.

37 Claims, 1 Drawing Sheet

FRAGRANCE EMITTING ARTICLE

The present invention relates to a fragrance emitting article. More particularly, the present invention relates to a fragrance emitting article with microcapsules containing a fragrance, which microcapsules are associated with the fragrance emitting article without the addition of a binder. The invention also relates methods of making the subject fragrance emitting articles and methods of using those articles.

People have long applied scents and fragrances to themselves and their garments for a variety of purposes including: to mask or enhance the natural odor of the user, to repel insects, to offer medicinal or therapeutic effects, etc. It is generally preferable to provide a scent and/or fragrance at a suitable intensity for a prolonged period of time. Notwithstanding, mixtures of perfumes or fragrance raw materials when deposited on the skin lose their intensity and may change their character with time, mainly due to factors such as differential evaporation and skin penetration.

Accordingly, it is desired to have a perfume emitting article suitable for wearing on any part of a user's clothing near where one would normally dab perfume. It is also desired to have a perfume emitting article suitable for inclusion in a magazine, in a pouch or on a postcard, to provide a fragrance sample for marketing purposes. With any of these uses, it would also generally be desirable for the fragrance emitting article to exhibit the ability to release a fragrance at a suitable intensity for an extended period of time. Additionally, it would often be desirable for the fragrance emitting article to exhibit the ability to be removably adhered to an article of clothing during the time fragrance is being released.

SUMMARY OF THE INVENTION

In a preferred embodiment of the present invention, fragrance emitting articles are provided, including: a support layer with a top surface and a bottom surface, wherein an adhesive is disposed on the bottom surface of the support layer and microcapsules containing a fragrance are dispersed on the top surface of the support layer. The microcapsules are preferably associated with the support layer without the addition of a binder.

In a preferred aspect of the present invention, the fragrance emitting articles include a release layer, wherein the adhesive is interposed between the bottom surface of the support layer and the release layer. Preferably, the release layer includes a layer of polyester film preferably with a release coating on at least that surface of the release layer which contacts the adhesive.

In another preferred aspect of the present invention, the support layer and the microcapsules are colored to be esthetically pleasing. Preferably, the support layer and the microcapsules will be colored such that the microcapsules are not distinguishable from the support layer by the naked eye.

In another preferred aspect of the present invention, the support layer exhibits a basis density of 0.5 to 3.0 ounces/square yard. Wherein the term "basis density" means the density of the support layer alone in the absence of the adhesive layer and the microcapsules.

In another preferred aspect of the present invention, the support layer includes a non-woven fabric. Preferably, the non-woven fabric includes polyester. Still more preferably, the non-woven fabric includes long chain polyester fibers comprising at least 85% by weight of an ester of a substituted aromatic carboxylic acid. Yet still more preferably, the polyester fibers include substituted terephthalic units and parasubstituted hydroxybenzoate units. Still even more preferably, the polyester fibers include at least one of polyethylene terepthalate; 1,4-cyclohylene-dimethylene terephthalate and polybutylene terephthalate.

In another preferred aspect of the present invention, the support layer includes polyester fibers having a tenacity in the range of 2.0 to 10.0 grams/denier and exhibits an elastic recovery of at least 65%, more preferably between 65% to 95%.

In another preferred aspect of the present invention, the support layer includes polyester fibers and has a density of 1.34 to 1.38 grams/cubic meter.

In another preferred aspect of the present invention, the support layer includes polyester fibers and exhibits a moisture regain of less than 0.4%.

In another preferred aspect of the present invention, the support layer includes polyester fibers and exhibits a melting point between 240 to 260° C.

In another preferred aspect of the present invention, the support layer includes polyester fibers having a diameter of 0.5 to 30 micrometers.

In another preferred aspect of the present invention, the support layer includes nylon. Preferably, the support layer includes nylon fibers having less than 85% of the amide linkages attached directly to the two aromatic rings. Yet still more preferably, the nylon fibers include at least one of nylon 6; nylon 6,6; nylon 6,9; nylon 6,10; nylon 6,12 and nylon 11.

In another preferred aspect of the present invention, the support layer includes nylon fibers having a tenacity in the range of 2.0 to 10.0 grams/denier.

In another preferred aspect of the present invention, the support layer includes nylon fibers and exhibits an elastic recovery after a two percent elongation of at least 95%, more preferably at least 98%, most preferably at least 99%.

In another preferred aspect of the present invention, the support layer includes nylon fibers and exhibits a density of 1.14 to 1.20 grams/cubic centimeter.

In another preferred aspect of the present invention, the support layer includes nylon fibers having a melting point between 200 and 270° C. and exhibits a moisture regain of 3.0 to 5.0%.

In another preferred aspect of the present invention, the support layer includes nylon fibers having a diameter of 0.5 to 30 micrometers.

In another preferred aspect of the present invention, the support layer includes randomly oriented nylon fibers.

In another preferred aspect, the fragrance emitting articles of the present invention include 60 to 98% fragrance by weight, more preferably at least 85% fragrance by weight.

In another preferred aspect of the present invention, the microcapsules include an outer shell composed of a water soluble polymer, more preferably a gelatin.

In another preferred aspect of the present invention, the microcapsules have an average diameter of 5 to 65 micrometers.

In another preferred aspect of the present invention, the fragrance emitting article includes at least 10 mg of fragrance/square inch of fragrance emitting article, more preferably between 10 and 90 mg of fragrance/square inch of fragrance emitting article.

In another preferred aspect of the present invention, the layer of microcapsules supported by the support layer is at least 0.5 mil thick.

In another preferred aspect of the present invention, the adhesive includes at least one of polyacrylic adhesive and polyisobutylene.

In another preferred embodiment of the present invention, a method for producing the fragrance emitting article of the present invention is provided, including: (a) coating an adhesive layer onto a release layer; (b) laminating the product of (a) onto a support layer; (c) coating an aqueous slurry of microcapsules containing a fragrance onto the support layer without the addition of a binder; and (d) drying the product of (c) while maintaining a temperature of less than 45° C. Preferably, the method may further include: (e) cutting the product of (d) into a desired size and shape; and, (f) locating the product of (e) in a pouch.

In another preferred embodiment of the present invention, a method for producing the fragrance emitting articles of the present invention is provided, including: (a) coating an adhesive layer onto a support layer; (b) coating an aqueous slurry of microcapsules containing a fragrance onto the support layer without the addition of a binder; and (c) drying the product of (b) while maintaining a temperature of less than 45° C. Preferably, the method may further include: (d) cutting the product of (c) into a desired size and shape; and (e) locating the product of (d) in a pouch.

In another preferred embodiment of the present invention, a method for an individual to wear a fragrance is provided, including: removably adhering a fragrance emitting article to a garment worn by the individual, preferably the fragrance emitting article is removably adhered to a garment surface which facilitates minimal contact with the skin of the individual; wherein the fragrance emitting article comprises a support layer with a top surface and a bottom surface; wherein an adhesive layer is disposed on the bottom surface and wherein microcapsules containing a fragrance are dispersed on the top surface without a binder.

BRIEF DESCRIPTION OF THE DRAWINGS

There are shown in the drawings certain exemplary embodiments of the present invention as presently preferred. It should be understood that the present invention is not limited to the embodiments disclosed as examples, and is capable of variation within the spirit and scope of the appended claims.

In the drawings.

DETAILED DESCRIPTION

Figure 1:
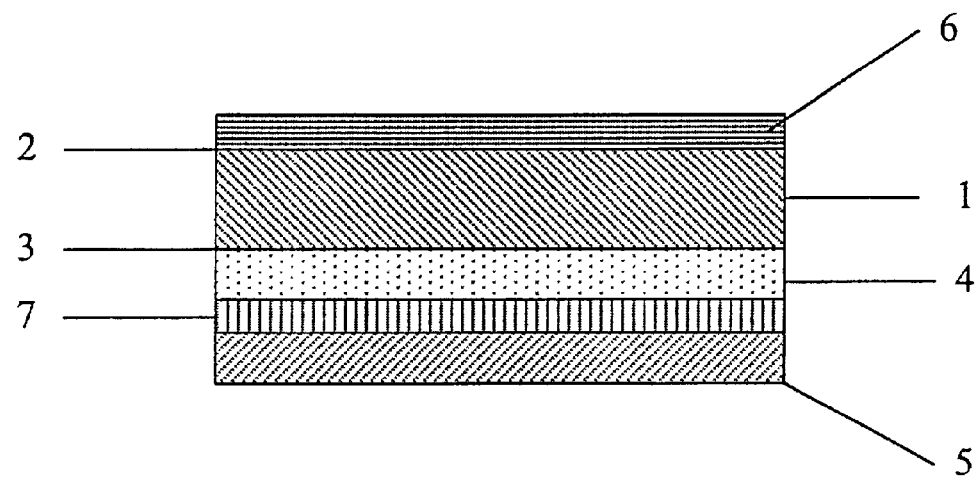
FIG. 1 is a depiction of a cross-sectional, side elevational view of a preferred fragrance emitting article of the present invention.

The present invention provides fragrance emitting articles and methods of making and using the same. For example, the fragrance emitting articles of the present invention provide an effective tool whereby manufactures of perfumes can market those perfumes to prospective customers. Alternatively, the fragrance emitting articles of the present invention provide an effective tool whereby individuals can utilize fragrances for any one of a variety of purposes, including: masking offensive odors, for pleasure and for aromatherapy.

The preferred embodiments of the present invention will now be discussed with reference to FIG. 1 which generally depicts a preferred fragrance emitting article of the present invention containing a support layer 1 with an upper surface 2 and a lower surface 3, an adhesive layer 4 applied to the lower surface 3, an optional release layer 5, with an optional release coating 7, releasably applied over the adhesive 4, and a layer of encapsulated fragrance 6 supported by the support layer 1. One skilled in the art will recognize that there maybe some intermingling between the support layer and the adhesive layer at the interface between the support layer and the adhesive layer. Also, one skilled in the art will recognize that the layer of encapsulated fragrance may intermingle with the support layer at the interface between the support layer and the layer of encapsulated fragrance.

Materials suitable for use as the support layer 1 in the fragrance emitting articles of the present invention preferably include, but are not limited to, a non-woven fabric; more preferably, at least one of a polyester non-woven fabric and a nylon non-woven fabric; most preferably, at least one of a polyester non-woven fabric with a random filament orientation and a nylon non-woven fabric with a random filament orientation.

Polyester non-woven fabrics suitable for use in the support layer preferably include a non-woven fabric made from long chain polyester fibers containing at least 85% by weight of an ester of a substituted aromatic carboxylic acid. More preferably, the long chain polyester fibers include substituted terepthalic units and parasubstituted hydroxybenzoate units. Most preferably, the long chain polyester fibers include at least one of polyethylene terephthalate (PET); 1,4-cyclohylene-dimethylene terephthalate (PCDT); and polybutylene terephthalate (PBT).

Preferably, the polyester fibers used in the non-woven fabric of the support layer exhibit a tenacity within the range of 2.0 to 10.0 grams/denier. The polyester fibers used in the non-woven fabric of the support layer preferably exhibit a diameter ranging from 0.5 to 30 micrometers.

The polyester non-woven fabric suitable for use with the present invention preferably exhibits an elastic recovery after a two percent elongation of 65 to 95%. The density of the polyester non-woven fabric of the support layer preferably ranges from 1.34 to 1.38 grams per cubic centimeter. The support layer preferably exhibits a moisture regain of 0.4%. The support layer preferably exhibits a melting point within the range of 240 to 260° C.

Polyester non-woven fabric suitable for use with the present invention can be produced by any known method. For example, the polyester non-woven fabric may be produced through well known spunbond processes, meltblown processes or any combination thereof. In either a spunbond process, a meltblown process or any combination thereof, the polyester is initially supplied as a resin which is subsequently converted into continuous filaments through use of an extruder. The filaments are drawn to the desired denier through air currents or mechanical drawing. With the spunbond process, the filaments are then randomly deposited on a moving conveyor belt to form a web, which web may optionally be thermally bonded using, for example, any of the well known overall or point bonding techniques. With the meltblown process, the filaments are propelled with an air stream against a collecting screen where they form cohesive bonds with one another to form a randomly oriented, self-bonded fabric, which can optionally be thermally bonded using, for example, any of the well known overall or point bonding techniques.

Nylon non-woven fabric suitable for use with the present invention preferably include a non-woven fabric including long chain nylon fibers containing less than 85% amide linkages attached directly to the nylon aromatic rings. More preferably, the long chain nylon fibers contain at least one of nylon 6; nylon 6,6; nylon 6,9; nylon 6,10; nylon 6,12 and nylon 11. Nylon fibers suitable for use with the present invention, preferably exhibit a tenacity within the range of 2.0 to 10.0 grams/denier and have a diameter ranging from 0.5 to 30 micrometers.

Nylon non-woven fabric suitable for use with the present invention preferably exhibits an elastic recovery after a two percent elongation of at least 95%, more preferably at least 98%, most preferably at least 99%. The density of the nylon non-woven fabric preferably ranges from 1.14 to 1.20 grams per cubic centimeter. The nylon non-woven fabric preferably exhibits a moisture regain of 3.0 to 5.0% and preferably exhibits a melting point within the range of 200 to 270° C.

Nylon non-woven fabric suitable for use with the present invention can be produced by any known method. For example, the nylon non-woven fabric may be produced through well known spunbond processes, meltblown processes or any combination thereof. In the case of the use of either a spunbond process, a meltblown process or any combination thereof, the nylon is initially supplied as a resin which is subsequently converted into continuous filaments through use of an extruder. The filaments are drawn to the desired denier through air currents or mechanical drawing. With the spunbond process, the filaments are then randomly deposited on a moving conveyor belt to form a web, which web may optionally be thermally bonded using, for example, any of the well known overall or point bonding techniques. With the meltblown process, the filaments are propelled with an air stream against a collecting screen where they form cohesive bonds with one another to form a randomly oriented, self-bonded fabric, which can optionally be thermally bonded using, for example, any of the well known overall or point bonding techniques.

The support layer of the present invention preferably includes a non-woven fabric containing a multiplicity of randomly oriented fibers cohesively bound together into a self-bonded fabric. Optionally, the non-woven fabric can be thermally bonded using well known techniques including overall and point bonding techniques. Preferably, the non-woven fabric suitable for use with the present invention exhibits a basis weight ranging from 0.50 to 3.0 ounces per square yard. One skilled in the art will recognize that the basis weight of the non-woven fabric can be altered by, for example, changing the speed of the extrusion process used to produce the fibers of which the non-woven fabric is composed, changing the size of the spinnerets used in the extrusion process, changing the velocity and or direction of the air stream used to draw the fibers, and/or the die to collector distance.

Preferably, non-woven fabric suitable for use with the present invention is optionally colored to provide an esthetically pleasing appearance. Also, the fragrance emitting articles of the present invention may preferably be provided in any shape or design. The shape or design implemented will be dictated by the intended use for the fragrance emitting article. That is, the shape or design of the fragrance emitting article may be any which is compatible with the marketing concept for the given article. For example, a fragrance emitting article may be provided in the shape of a heart, a flower, an article of fruit, a circle, a diamond, a corporate logo, trademark, etc.

Materials suitable for use in the adhesive layer include any synthetic adhesive including both water born and solvent born adhesives. Suitable adhesives include pressure sensitive polyacrylic adhesives and polyisobutylene adhesives. One skilled in the art will know how to select an appropriate adhesive for any given application. For example, if the fragrance emitting article is to be removably applied to an article of clothing, the adhesive layer may preferably comprise a pressure sensitive adhesive such as a polyacrylic or a polyisobutylene adhesive, most preferably a water born polyacrylic polymer adhesive. A most preferred adhesive is available from Monsanto Chemical Company under the trademark GELVA 3011.

Materials suitable for use in the optional release layer include materials impermeable to the constituents of the adhesive layer and which are easily stripped off or released prior to use of the fragrance emitting articles of the present invention. Preferably, the release layer includes at least one of silicon, polyvinyl chloride, polyester, polyvinylidene chloride, polystyrene, polyethylene and paper; more preferably, at least one of silicone and polyester. The release layer may preferably also include an optional release coating, for example siliconized polyester film.

Encapsulated fragrance suitable for use with the present invention include rupturable microcapsules containing a fragrance. A wide variety of processes for the manufacture of microcapsules are known. These varied processes provide different techniques for making microcapsules of varying sizes, with different shell materials and with different encapsulated materials. Rupturable microcapsules suitable for use with the present invention preferably range in size from 5 to 65 micrometers in diameter. Optionally, the rupturable microcapsules may be colored with any pigment or oil soluble dyes, most preferably, the rupturable microcapsules are colored to blend with the coloring of the support layer. Rupturable microcapsules suitable for use with the present invention preferably include an outer shell containing at least one of a gelatin and a water soluble polymer suitable for use as an encapsulating substance, most preferably a gelatin. The rupturable microcapsules suitable for use with the present invention preferably include 60 to 98% fragrance, more preferably at least 85% fragrance, most preferably about 93.5% fragrance.

Fragrances suitable for use with the present invention preferably include oil soluble fragrance concentrates in the absence of polar solvents such as alcohol, glycol, etc. Preferably, the fragrance incorporated into the rupturable microcapsules of the present invention evaporates through the walls of the rupturable microcapsules over time. Preferably, the rupturable microcapsules have varying wall thicknesses to facilitate a controlled release of fragrance from the fragrance emitting article over time. The user of the fragrance emitting articles of the present invention can manually increase the rate of release of fragrance therefrom by breaking some of the microcapsules by, for example, by rubbing or scratching the surface of the fragrance emitting article.

The volume of encapsulated fragrance incorporated into the fragrance emitting articles of the present invention can be varied over a wide range, depending on such factors as the intensity of the odor desired for a given application and the intended useful life of the fragrance emitting article. Generally, it will be desirable to incorporate a high level of encapsulated fragrance in the fragrance emitting articles of the present invention to obtain a long useful life, preferably eight to twenty-four hours, more preferably at least twelve hours. Preferably, the fragrance emitting articles of the present invention will have a layer of rupturable microcapsules at least one half mil thick and will preferably include from 10 to 90 mg of fragrance per square inch of fragrance emitting article.

Another preferred embodiment of the present invention provides a method for producing the fragrance emitting articles of the present invention, including: (a) coating an adhesive layer onto a release layer; (b) laminating the product of (a) onto a support layer; (c) coating an aqueous slurry of microcapsules containing a fragrance onto the support layer without the addition of a binder; and (d) drying the product of (c) while maintaining a temperature of less than 45° C. Preferably, the method may further include: (e) cutting the product of (d) into a desired size and shape; and, (f) locating the product of (e) in a pouch.

Another preferred embodiment of the present invention provides a different method for producing the fragrance emitting articles of the present invention, including: (a) coating an adhesive layer onto a support layer; (b) coating an aqueous slurry of microcapsules containing a fragrance onto the support layer without the addition of a binder; and (c) drying the product of (b) while maintaining a temperature of less than 45° C. Preferably, the method may further include: (d) cutting the product of (c) into a desired size and shape; and (e) locating the product of (d) in a pouch.

Given the nature of the fragrance emitting articles of the present invention a multitude of uses for such articles will be readily apparent to one skilled in the art. For example, the fragrance emitting articles of the present invention may be used as fragrance sampling devices provided in magazines, in department stores, or through direct marketing (for examples on post cards distributed to prospective fragrance customers), which sampling devices can, for example, be removed from the magazine or post card and placed directly onto the clothes of a prospective fragrance consumer where the article can be worn and enjoyed for several hours or all day. The fragrance emitting articles of the present invention also provide a way of wearing fragrances for, for example, pleasure and aromatherapy. Specifically, the fragrance emitting articles of the present invention allow an individual to wear a fragrance without applying that fragrance to ones skin. It is known that skin chemistry may affect the odor exhibited by a fragrance and in some cases may result in an adverse reaction, for example the development of a rash at the site of application. Accordingly, the fragrance emitting devices of the present invention provide a safe method of wearing/using a fragrance with a minimized potential for negative side effects associated with the application of a fragrance to the skin and provides a truer fragrance odor with a minimized potential for skin chemistry affects.

The present invention having been disclosed in connection with the foregoing embodiments, additional embodiments will now be apparent to persons skilled in the art. The present invention is not intended to be limited to the embodiments specifically mentioned, and accordingly reference should be made to the appended claims rather than the foregoing discussion, to assess the spirit and scope of the present invention in which exclusive rights are claimed.

We claim:

1. A fragrance emitting article comprising a support layer with a top surface and a bottom surface; wherein an adhesive layer is disposed on the bottom surface; wherein microcapsules comprising an outer shell and an encapsulated fragrance are dispersed on the top surface without a binder; wherein the outer shell comprises a water soluble polymer; wherein the fragrance is oil soluble; and wherein the support layer is a non-woven fabric which is point bound or overall bound.

2. The fragrance emitting article of claim 1, further comprising a release layer; wherein the adhesive layer is interposed between the bottom surface and the release layer.

3. The fragrance emitting article of claim 2, wherein the release layer comprises a polyester film with a release coating.

4. The fragrance emitting article of claim 1, wherein the microcapsules are colored.

5. The fragrance emitting article of claim 1, wherein the support layer is point bound.

6. The fragrance emitting article of claim 5, wherein the non-woven fabric comprises a polyester fiber.

7. The fragrance emitting article of claim 6, wherein non-woven fabric comprises long chain polyester fibers comprising at least 85% by weight of an ester of a substituted aromatic carboxylic acid.

8. The fragrance emitting article of claim 7, wherein the polyester fibers comprise substituted terephthalic units and parasubstituted hydroxybenzoate units.

9. The fragrance emitting article of claim 7, wherein the polyester fibers comprise at least one of polyethylene terepthalate; 1,4-cyclohylene-dimethylene terephthalate and polybutylene terephthalate.

10. The fragrance emitting article of claim 7, wherein the polyester fibers exhibit a tenacity in the range of 2.0 to 10.0 grams/denier and wherein the non-woven fabric exhibits an elastic recovery of at least 65%.

11. The fragrance emitting article of claim 10, wherein the non-woven fabric exhibits an elastic recovery in the range of 65% to 95%.

12. The fragrance emitting article of claim 7, wherein the non-woven fabric has a density of 1.34 to 1.38 grams per cubic centimeter.

13. The fragrance emitting of claim 7, wherein the non-woven fabric exhibits a moisture regain of less than 0.4%.

14. The fragrance emitting article of claim 7, wherein the polyester fibers have a melting point of 240 to 260° C.

15. The fragrance emitting article of claim 7, wherein the polyester fibers have a diameter of 0.5 to 30 micrometers.

16. The fragrance emitting article of claim 7, wherein the polyester fibers are randomly oriented in the support layer.

17. The fragrance emitting article of claim 5, wherein the non-woven fabric comprises a nylon fiber.

18. The fragrance emitting article of claim 17, wherein the non-woven fabric comprises nylon fibers having less than 85% of the amide linkages attached directly to the two aromatic rings.

19. The fragrance emitting article of claim 18, wherein the nylon fibers comprise at least one of nylon 6; nylon 6,6; nylon 6,9; nylon 6,10; nylon 6,12 and nylon 11.

20. The fragrance emitting article of claim 19, wherein nylon fibers exhibit a tenacity of 2.0 to 10.0 grams/denier.

21. The fragrance emitting article of claim 19, wherein the non-woven fabric exhibits an elastic recovery of at least 99% after a two percent elongation.

22. The fragrance emitting article of claim 19, wherein the non-woven fabric has a density of 1.14 and 1.20 grams/cubic centimeter.

23. The fragrance emitting article of claim 19, wherein the non-woven fabric exhibits a moisture regain of 3.0 to 5.0% and a melting point between 200 and 270° C.

24. The fragrance emitting article of claim 18, wherein the nylon fibers have a diameter of 0.5 to 30 micrometers.

25. The fragrance emitting article of claim 18, wherein the nylon fibers are randomly oriented in the support layer.

26. The fragrance emitting article of claim 1, wherein the support layer exhibits a basis density of 0.5 to 3.0 ounces/square yard.

27. The fragrance emitting article of claim 1, wherein the microcapsules comprise 60 to 98% by weight fragrance.

28. The fragrance emitting article of claim 1, wherein the microcapsules comprise at least 85% by weight fragrance.

29. The fragrance emitting article of claim 1, wherein the microcapsules have an average diameter of 5 to 65 micrometers.

30. The fragrance emitting article of claim 1, wherein the support layer supports a layer of microcapsules at least 0.5 mil thick.

31. The fragrance emitting article of claim 1, wherein the adhesive layer comprises at least one of a polyacrylic adhesive and polyisobutylene.

32. The fragrance emitting article of claim 1, wherein the water soluble polymer comprises a gelatin.

33. A fragrance emitting article comprising a support layer with a top surface and a bottom surface; wherein an adhesive layer is disposed on the bottom surface; wherein microcapsules containing a fragrance are dispersed on the top surface without a binder; wherein the support layer is a non-woven fabric; and, wherein the microcapsules comprise a shell comprised of a water soluble polymer and the contained fragrance is oil soluble.

34. The fragrance emitting article of claim 33, wherein polymer comprises a gelatin.

35. A fragrance emitting article comprising a support layer with a top surface and a bottom surface; wherein an adhesive layer is disposed on the bottom surface; wherein microcapsules containing a fragrance are dispersed on the top surface without a binder; and, wherein the fragrance emitting article contains at least 10 mg of fragrance/square inch of fragrance emitting article.

36. The fragrance emitting article of claim 35, wherein the fragrance emitting article contains between 10 and 90 mg of fragrance/square inch of fragrance emitting article.

37. A method for an individual to wear a fragrance, comprising removably adhering a fragrance emitting article to a garment, wherein the fragrance emitting article comprises a support layer with a top surface and a bottom surface; wherein an adhesive layer is disposed on the bottom surface to facilitate removably adhering the fragrance emitting article to the garment and wherein microcapsules containing a fragrance are dispersed on the top surface without a binder.

* * * * *